United States Patent [19]

Rossmark

[11] Patent Number: 4,880,410
[45] Date of Patent: Nov. 14, 1989

[54] DISPOSABLE SYRINGE

[75] Inventor: Rene T. M. Rossmark, Amsterdam, Netherlands

[73] Assignee: NV Medicopharma, Zaandam, Netherlands

[21] Appl. No.: 183,852

[22] Filed: Apr. 20, 1988

[30] Foreign Application Priority Data

Apr. 21, 1987 [NL] Netherlands ............... 8700947

[51] Int. Cl.4 ............................................. A61M 5/00
[52] U.S. Cl. ..................................... 604/110; 604/218
[58] Field of Search ................ 604/110, 111, 187, 218

[56] References Cited

U.S. PATENT DOCUMENTS 4,687,467  8/1987  Cygielski ..................... 604/110
4,699,614 10/1987  Glazier ........................ 604/110

FOREIGN PATENT DOCUMENTS 2298340  8/1976  France ........................ 604/110

Primary Examiner—John D. Yasko
Attorney, Agent, or Firm—Helfgott & Karas

[57] ABSTRACT

A disposable syringe for medicinal or similar purposes, of the type, which may be used once only. The piston rod is coupled to the piston through a lost-motion connection. The piston and the piston rod are initially positioned one relative to the other such, that they are—as seen in the moving out direction—rigidly coupled. In the end portion of the cylinder turned away from the injection needle means are provided adapted to lock the piston and the piston rod in said rigid coupling position along a part of the suction stroke length corresponding to the length of said cylinder end portion, such that upon initiating the injection stroke a certain lost motion of the piston rod relative to said piston will occur only after the area comprising said locking means has been passed through, said lost motion causing said piston to become in a state, from which a next effective suction stroke is impossible.

8 Claims, 2 Drawing Sheets

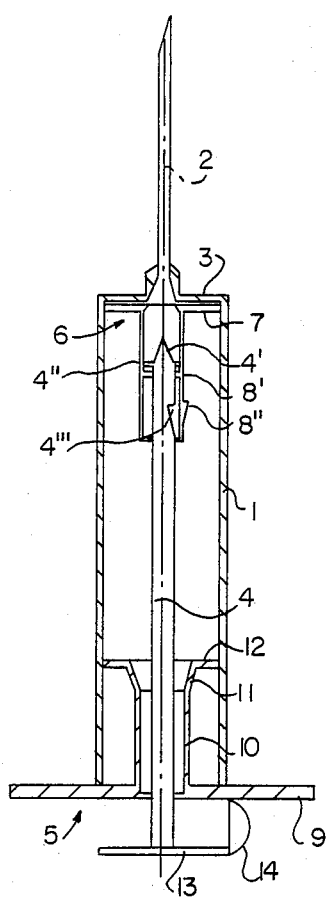
FIG. IA
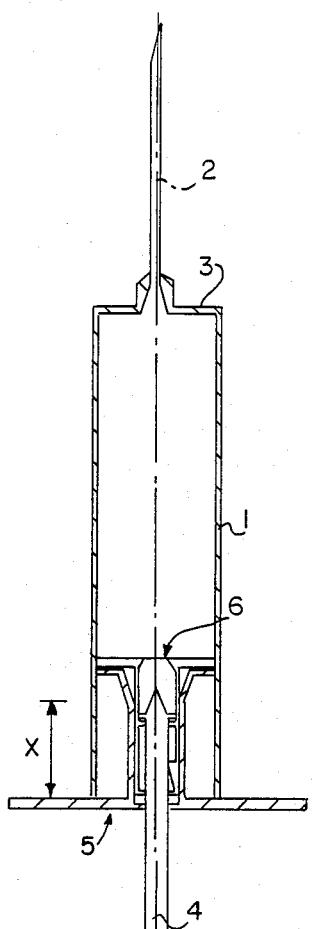
FIG. IB
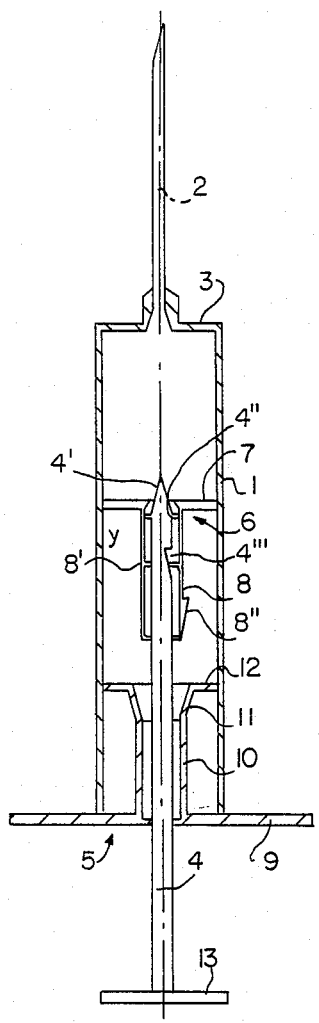
FIG. IC

DISPOSABLE SYRINGE

The invention relates to a disposable syringe for medicinal or similar purposes, of the type, with which the piston may be moved out from a starting position within the syringe cylinder only once to suck a dose of injection liquid, may thereafter be returned into the cylinder for carrying out an injection and is, at the end of the injection stroke, in a position which makes it impossible to carry out another effective suction stroke.

Syringes of this type are known from FR-A-2.2.181.580, as well as from NL-A-7314940 and NL-A-7901872.

In the well-known embodiment according to said French patent application a spring blade ring member is provided in the transitional area between piston and piston rod, the outer diameter of which ring, in untensioned condition, is somewhat larger than the inner diameter of the syringe cylinder. In the starting position—being the position in which the syringe, in a sterile packing, is delivered for first and sole use—the spring blade ring is in a pretensioned state and takes such a position in the transitional area between piston and piston rod, that its outer circumferential edge is trailing relative to its inner circumferential edge, as seen in the moving out direction. In this position the spring blade ring does not impede the retracting movement of the piston. At the end of this movement—the suction stroke—the spring blade ring has arrived in a position opposite to an annular widening of the cylinder so that it is permitted to relieve by taking its flat, untensioned shape. When moving the piston in again—the injection stroke—the spring blade ring leaves the annular widening and is forced to contract within the (smallest) cylinder diameter.

Thus the annular widening of the cylinder at the cylinder end turned away from the needle enables the spring blade ring to bend over from a position not impeding the retracting movement to a position not impeding the inward movement of the piston.

At the end of the injection storke, however, such a bend over will not be possible. the circumferential edge of the pretensioned ring will now bite into the cylinder wall, if one attempts to move the piston out for a next suction stroke. In this manner in principle an effective safeguard against reuse of the syringe could be obtained. The measures taken for that purpose, however, have certain disadvantages, which affect the practical usability of the syringe.

In the first place it will be difficult to place the piston with the spring blade ring in the correct position within the syringe cylinder in the starting position of the latter. It will be clear, that an introduction through the cylinder end turned away from the injection needle - being the usual manner of assembling—is not possible. The only possibility seems to be, that the cylinder end facing the injection needle is closed by means of a separate end cover (containing the needle) after having introduced the piston through the still open cylinder end. This, however, means a larger number of parts and a more complicate way of assembling.

A further objection concerns the use of the syringe. After having sucked the desired dose of injection liquid it is usual and for intravenous administration even necessary to expel the air before performing an injection. This is accomplished by holding the syringe with the needle directing upwardly, "touching" the syringe cylinder to cause the air bubbles to rise and then pushing the piston into the cylinder to such an extent that a small quantity of liquid is discharging from the needle. The syringe is then ready for performing an injection.

Upon introducing the needle into the body it has to be checked whether the needle tip is actually located within a blood vessel (in case of an intravenous administration) or not (in case of a intramuscular administration). For this purpose the syringe cylinder is retracted through a certain distance or moved back and forth while the piston is retracted a little from the syringe cylinder to create a slight underpressure within the cylinder. The appearance of blood in the portion of the needle projecting out of the body is to be seen as an indication that the needle tip is indeed within a blood vessel.

A way of handling just referred to will, in general, not be possible with the well-known syringe above referred to. For during the preceding deaeration of the filled syringe the spring blade ring will have "bent over", due to which it will not be possible anymore to retract the piston for creating a certain underpressure.

In the well-known syringe according to NL-A-7314940 the piston body has a spring-loaded cutter member, which remains inactive during the performance of the suction stroke but which will penetrate into the cylinder wall and cut the same through when the piston is moved in. This well-known embodiment is relatively complicated and in addition to that involves a substantial increase of the resistance to be overcome when performing the injection stroke. This makes the syringe less handlable for the one who carries out the injection. Moreover the cutting through would already occur during the deaeration of the syringe, i.e. at a moment at which the proper injection has to be started yet. This, of course, limits the possibility of manoeuvring (pulling back) of the piston immediately preceding the proper injection stroke.

Finally, with the syringe according to NL-A-7901872 the piston is blocked or becomes inactive at the end of the maximum injection stroke as a result of a radially springy circumferential portion of the piston engaging a corresponding recess in the cylinder wall and being held therein. A serious drawback of this embodiment is, that the piston has to be moved in beyond its starting position to have the desired anti-reuse effect occur. Consequently, of this condition is not fulfilled the syringe can be simply reused.

The invention aims at overcoming the above disadvantages and drawbacks of the well-known syringes. According to the invention this aim is achieved in that the piston rod is coupled to the piston through a lost-motion connection, the piston and the piston rod being initially positioned one relative to the other such, that they are—as seen in the moving out direction—rigidly coupled, means being provided in the end portion of the cylinder turned away from the injection needle which are adapted to lock said piston and said piston rod in said relative rigid coupling position along a part of the suction stroke length corresponding to the length of said cylinder end portion, such that upon initiaing the injection stroke a certain lost motion of the piston rod relative to said piston will occur only after the area comprising said locking means has been passed through, said lost motion causing said piston to become in a state, from which a next effective suction stroke is impossible.

The locking zone enables to manoeuvre the piston in the above manner before carrying out the proper injection stroke. As soon as the locking zone, during the performance of the injection stroke, has been passed through and as a consequence thereof the mutual locking of piston and piston rod is released, a linear displacement of the piston rod relative to the piston along a distance corresponding to the length of the lost motion is taking place, which, while the injection storke has hardly begun, renders the piston inoperative as a suction means for a next suction stroke.

The length of the lost motion may be a fraction of the manoeuvring length determined by the locking zone.

In a practical embodiment the end of the piston rod facing towards the needle is thorn-shaped, whereas at least the central portion of the end face of the piston is formed by a membrane, such that in the initial phase of the injection stroke the thorn-shaped piston rod end will penetrate into the membrane, however, without establishing a communication between the cylinder space in front of and behind the piston respectively.

Thus the membrane portion of the piston will be perforated already in an early stage, but this does not influence the injection stroke. When the piston is moved out, however, the thorn-shaped piston rod end will retract from the perforation in the membrane and a communication between the cylinder spaces in front of and behind the piston will be established, due to which any further sucking of injection liquid is excluded.

In a second practical embodiment the piston comprises two parts having mutually engaging end faces which extend along corresponding helical lines, one of said parts being fixedly connected to the piston rod, said parts being turned one relative to the other in a direction opposite to the winding direction of the helical lines so as to take—in the starting position—a mutual angular position at which the piston has a maximum length, while the locking means in the cylinder and portion are formed by axial ribs, which prevent the two piston parts from turning one relative to the other from said initial angular position, the pitch of the helical lines being so large, that the two piston parts may—under axial pressure and simultaneous shortening of the total piston length—be turned one relative to the other in a direction corresponding to the winding direction of the helical lines, the latter mutual turning movement breaking the axial coupling between the two piston parts.

The inventions will be hereinafter further explained with reference to the drawing which shows two examples.

FIG. 1A–1C show a longitudinal section through the disposable syringe according to the invention in a first embodiment, whereby the syringe is shown in the initial position (1A), at the end of the suction stroke (1B) and in a situation during the injection stroke (1C) respectively;

Figure 2A:
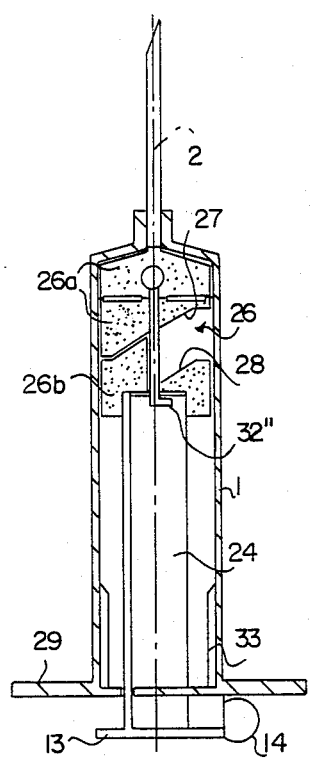
FIG. 2A–2C show a modification of the embodiment according to FIG. 1, in the initial position (2A), at the end of the suction stroke (2B) and at the end of the injection stroke (2C) respectively

In FIG. 1A–1C designates the syringe cylinder, formed e.g. from plastics material, one end of which is closed by an end wall 3 carrying the injection needle 2, and at the other end of which a cover 5 of special construction is provided through which the piston rod 4 extends. The piston 6 comprises a disc-shaped portion 7 of a suitable, pierceable plastics or rubber-like material, and a tubular portion 8 connected therewith, in which the end portion of the piston rod 4 facing the needle 2 is housed. The latter piston rod portion terminates in a thorn-shaped tip 4' and has a collar 4", which cooperates with an inner circumferential shoulder 8' of the tubular portion 8. A part of the wall of the tubular portion 8 is formed as a locking cam 8", which may take an inoperative position in which it projects in an untensioned state outwardly (vide FIG. 1A and 1C) but may be pressed inwardly so as to cooperate with a corresponding recess 4''' in a section of the piston rod 4 located within the tubular portion 8.

The cover is formed by an end wall 9, which at the same time serves as a finger lug and engages the terminal edge of the syringe cylinder 1. The end wall 9 carries a tubular portion 10 extending into the cylinder 1 and the inner diameter of which corresponds with the outer diameter of the tubular piston portion 8. The tubular portion 10 terminates at its inner end through a conical widening 11 into a flange 12, the outer circumferential edge of which engages the inner wall of the syringe cylindre 1. The angle of inclination of the widening 11 corresponds with that of the outer edge of the locking cam 8" in the inoperative position of the latter (FIG. 1A and 1C). The syringe is usually delivered—while in a sterile pack—in the initial state shown in FIG. 1A, in which a break-away strip 14 is provided between the cover 5 and the finger lug 13 on the free piston rod end. This break-away strip prevents a premature undesired piercing of the disc-shaped piston portion 7 by the thorn-shaped piston rod end 4', but will easily tear off when the piston is poulled.

The operation of the syringe above described is as follows:

When moving the piston from the initial position according to FIG. 1A towards the position according to FIG. 1B injection liquid may be sucked through the needle 2. During the major part of the suction stroke the locking cam 8" is located opposite the locking recess 4''' without, however, engaging the same. In the terminal phase of the suction stroke—when the tubular piston portion 8 enters into the tubular portion 10, the conically widened portion 11 of said tubular portion will press the locking cam 8" into engagement with the recess 4'''. From that moment onwards the piston rod and the piston are rigidly coupled also in the moving-in direction. This situation remains as long as the locking nock 8" is located within the tubular portion 1 and consequently is taking its operative position. This means, that the piston may be freely reciprocated along the trajectory indicated at x in order to deaerate the syringe after filling and create a slight underpressure during the injection phase.

Thus as soon as—during the movement from the position shown in FIG. 1B towards that according to FIG. 1C—the cam 8' has arrived beyond the trajectory x, said cam will enter into its inoperative position out of engagement with the recess 4''' and the piston rod 4 will then carry out a certain lost motion relative to the piston 6 before taking the piston along for the performance of the proper injection stroke. During this lost motion, the length of which is indicated at y in FIG. 1C, the thorn-shaped tip 4' of the piston rod will penetrate the membrane-like central portion of the disc-shaped piston portion 7. This penetration will not influence the further course of the injection stroke, due to the fact that the thorn-shaped tip 4' after having perforated the piston portion 7, will keep the perforaton closed in the direction of the injection stroke. However, as soon as the piston is poulled back, e.g. in an attempt to carry out a next suction stroke, the tip 4' is released from the perforation so that the two cylinder spaces in front of and behind the piston respectively become connected with each other, and no effective sucking will be possible anymore. In the above it is assumed that piston and piston rod will not turn one relative to the other. If such mutual turning movement is possible, the locking recess 4''' should be formed e.g. as a circumferential groove.

The embodiment shown in FIG. 2A–C will be hereinafter described only in sofar as the construction differs from that according to FIG. 1A–C. Parts corresponding with those in FIG. 1A–C have been indicated by the same reference numbers.

Figure 2B:
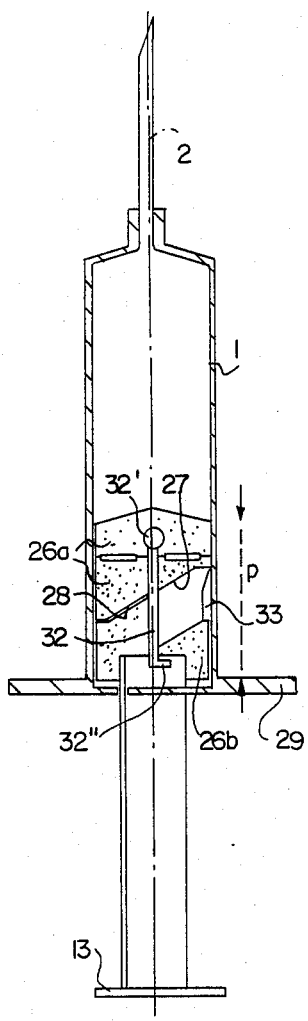
Figure 2C:
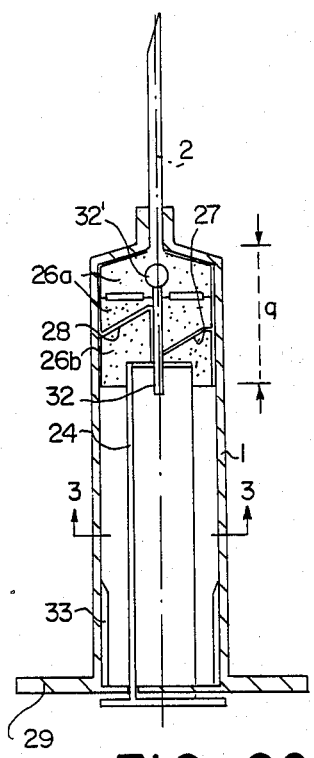
Figure 3A:
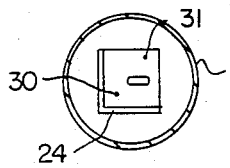
FIG. 3A and 3C show a cross-sectional view according to line III—III in FIG. 2A and 2C respectively.
Figure 3C:
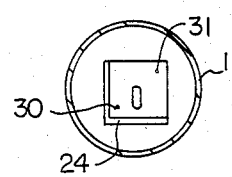

In the modification according to FIG. 2 and 3 the piston rod is formed by a length of angle section 24, which is guided in a correspondingly shaped slit in the finger lug 29, so that the piston rod is prevented from turning relative to the cylinder 1.

The piston 26 mainly consists of two parts 26a and 26b, the facing and engaging end faces 27 and 28 respectively of which extend along corresponding helical lines with a rather large pitch. The piston part 26b is rigidly connected with the piston rod 24.

In the initial state shown in FIG. 2A the piston parts 26a and 26b engage one another along a part only of the circumferential length of the end faces 27 and 28. The piston parts 26a and 26b cover a maximum piston length p, which is delimited by the coupling hook 32, the upper end 32' of which is anchored in the piston part 26a while the hook-shaped end 32'' of it engages, via a passage opening 30, behind a connecting plate 31 between piston rod 24 and piston part 26b (vide FIG. 3A). The sucking of the desired dose of injection liquid through the needle is effected by moving the piston from the initial position of FIG. 4A towards the position of FIG. 2B. In the terminal phase of this movement the two piston parts 26a and 26b engage a number of ribs 23 projecting inwardly from the cylinder wall. Said ribs prevent the piston parts 26a and 26b from turning one relative to the other along a certain "manoeuvring" trajectory which trajectory extends from the completely retracted position in FIG. 2B.

In the lower part of the syringe cylinder the piston 26 may thus be reciprocated. The anti-re-use effect will be initiated after the piston part 26a has become—at the start of the proper injection stroke towards the position of FIG. 2C—out of engagement with the ribs 33. From that moment onwards the injection pressure will cause the piston part 26a to turn in the winding direction of the helical lines relative to the piston part 26b until the total piston length of the piston parts 26a and 26b has reached the minimum length q (vide FIG. 2C). This relative turning movement is e.g. as large as a quarter of a complete turn. In case of a single helical line this means a lost motion of 5 mm when a pitch of 20 mm is used. As a result of the quarter turn of the piston rod 26a the hook shaped end 32'' has made a quarter of a turn as well and as a consequence thereof has become out of engagement with the connecting plate 31. This means that, when the piston rod 24 is then pulled from the end position of FIG. 2C the piston part 26a will not be taken along, so that a next dose of injection liquid cannot be sucked.

What is claimed is:

1. A disposable syringe for medicinal or similar purposes, comprising a cylinder, an injection needle, a piston and a piston rod, and in which the piston may be moved out from a starting position within the syringe cylinder only once to suck a dose of injection liquid, and may thereafter be returned into the cylinder for carrying out an injection, whereas at the end of the injection stroke, the piston will enter into a position which makes it impossible to carry out another effective suction stroke, the syringe further comprising lost-motion connections means coupling the piston and the piston rod, said connection means being initially positioned so that the piston and the piston rod, as seen in the moving out direction are directly coupled; and locking means provided in an end portion of the cylinder turned away from the injection needle, said locking means being adapted to lock said piston and said piston rod in the direct coupling position along the initial portion of the injection stroke length corresponding to the length of said end portion of said cylinder such that, upon initiating of the injection stroke, a certain lost motion of the piston rod relative to said piston will take place only after a region of said cylinder comprising said locking means has been passed through.

2. Syringe according to claim 1, wherein an end of said piston rod facing towards the injection needle is thorn-shaped.

3. syringe according to claim 2, wherein at least a central portion of an end face of the piston is formed by a membrane, such that in the initial phase of the injection stroke, after having passed through the locking means region, the thorn-shaped end of said piston rod will penetrate into the membrane, however, without establishing a communication between a cylinder space in front of and behind the piston, respectively.

4. Syringe according to claim 3, wherein the piston comprises a disc-shaped portion which contains the membrane, and a tubular portion connected therewith, which the end portion of the piston rod facing the needle is housed, said piston rod end portion having a collar behind the thorn-shaped end, said collar engaging, as seen in the moving-out direction, an inner circumferential shoulder of said tubular portion, a part of a wall of said tubular portion being formed as a locking cam, which may take an inoperative position, in which it projects in an untensioned state outwardly but may be pressed inwardly so as to cooperate with a corresponding locking recess in a section of the piston rod located within the tubular portion, the cylinder being closed by an end wall through which the piston rod extends and which carries a tubular portion extending into the cylinder and adapted to house the tubular portion of said piston in the fully retracted position of the piston, thereby pressing the locking cam into operative engagement with the locking recess in the piston rod.

5. Syringe according to claim 1, wherein the piston comprises two parts having mutually engaging end faces which extend along corresponding helical lines, one of said parts being fixedly connected to the piston rod, said parts being turned one relative to the other in a direction opposite to the winding direction of the helical lines so as to take, in the starting position, a mutual angular position at which the piston has a maximum length, while the locking means in the end portion of said cylinder are formed by axial ribs, which prevent the two piston parts from turning one relative to the other from said mutual angular position, the pitch of the helical lines being so large, that the two piston parts may, under axial pressure and simultaneous shortening of the total piston length be turned one relative to the other in a direction corresponding to the winding direction of the helical lines, the mutual turning movement breaking an axial coupling between the two piston parts.

6. In a disposable syringe for medicinal or similar purposes, of the type, with which the piston may be moved out from a starting position within a syringe cylinder only once to suck a dose of injection liquid, may thereafter be returned into the cylinder for carrying out an injection and is, at the end of the injection stroke, in a position which makes it impossible to carry out another effective suction stroke, the improvement comprising a piston rod being coupled to the piston through a lost-motion connection, the piston and the piston rod being initially positioned one relative to another such, that they are, as seen in the moving out direction, rigidly coupled; and locking means provided in an end portion of the cylinder turned away from an injection needle, said locking means being adapted to lock said piston and said piston rod in said rigid coupling position along a part of the suction stroke length corresponding to the length of said cylinder end portion, such that, upon initiating the injection stroke, a certain lost motion of the piston rod relative to said piston will occur only after a region comprising said locking means has been passed through, said lost motion causing said piston to be in a state, from which a next effective suction is impossible, the end of the piston rod facing towards the needle being thorn-shaped, and at least a central portion of the end face of the piston being formed by a membrane, such that in the initial phase of the injection storke, after having passed through the locking means region, the thorn-shaped piston rod end will penentrate into the membrane, however, without establishing a communication between a cylinder space in front of and behind the piston, respectively.

7. Syringe according to claim 6, wherein the piston comprises a disc-shaped portion which contains the membrane, and a tubular portion connected therewith, in which the end portion of the piston rod facing the needle is housed, said piston rod end portion having a collar behind the thorn-shaped end, said collar engaging, as seen in the moving-out direction, an inner circumferential shoulder of said tubular portion, a part of a wall of said tubular portion being formed as a locking cam, which may take an inoperative position, in which it projects in an untensioned state outwardly but may be pressed inwardly so as to cooperate with a corresponding locking recess in a section of the piston rod located within the tubular portion, the cylinder being closed by an end wall through which the piston rod extends and which carries a tubular portion extending into the cylinder and adapted to house the tubular portion of said piston in the fully retracted position of the piston, thereby pressing the locking cam into operative engagement with the locking recess in the piston rod.

8. Syringe according to claim 6, wherein the piston comprises two parts having mutually engaging end faces which extend along corresponding helical lines, one of said parts being fixedly connected to the piston rod, said parts being turned one relative to the other in a direction opposite to the winding direction of the helical lines so as to take, in the starting position, a mutual angular position at which the piston has a maximum length, while the locking means in the end portion of said cylinder are formed by axial ribs, which prevent the two piston parts from turning one relative to the other from said mutual angular position, the pitch of the helical lines being so large, that the two piston parts may, under axial pressure and simultaneous shortening of the total piston length, be turned one relative to the other in a direction corresponding to the winding direction of the helical lines, the mutual turning movement breaking an axial coupling between the two piston parts.

* * * * *